United States Patent
Scavilla et al.

(10) Patent No.: US 12,263,088 B2
(45) Date of Patent: Apr. 1, 2025

(54) EXPANDABLE HIP STEM

(71) Applicant: GLOBUS MEDICAL, INC., Audubon, PA (US)

(72) Inventors: Daniel Scavilla, Berwyn, PA (US); Marius Cobani, Southampton, PA (US); John Loiacono, Collegeville, PA (US); Kenny Chen, Philadelphia, PA (US); David Stumpo, Trappe, PA (US)

(73) Assignee: Globus Medical, Inc., Audubon, PA (US)

( * ) Notice: Subject to any disclaimer, the term of this patent is extended or adjusted under 35 U.S.C. 154(b) by 323 days.

(21) Appl. No.: 17/661,292

(22) Filed: Apr. 29, 2022

(65) Prior Publication Data

US 2023/0346565 A1 Nov. 2, 2023

(51) Int. Cl.
*A61F 2/36* (2006.01)
*A61F 2/30* (2006.01)

(52) U.S. Cl.
CPC ............ *A61F 2/367* (2013.01); *A61F 2/3676* (2013.01); *A61F 2002/30336* (2013.01); *A61F 2002/30616* (2013.01); *A61F 2220/0025* (2013.01)

(58) Field of Classification Search
CPC .. A61F 2002/30545; A61F 2002/30553; A61F 2002/30556; A61F 2002/30507; A61F 2/367; A61F 2/3676; A61F 2002/30336; A61F 2002/30616
See application file for complete search history.

(56) References Cited

U.S. PATENT DOCUMENTS

| | | | | |
|---|---|---|---|---|
| 3,024,785 A | * | 3/1962 | Dobelle | A61F 2/3662 623/23.26 |
| 3,760,802 A | * | 9/1973 | Fischer | A61B 17/7266 411/50 |
| 3,846,846 A | * | 11/1974 | Fischer | A61F 2/3662 411/33 |
| 4,520,511 A | * | 6/1985 | Gianezio | A61F 2/3609 623/22.46 |
| 4,756,711 A | * | 7/1988 | Mai | A61F 2/3676 623/23.26 |
| 4,911,722 A | * | 3/1990 | Crespy | A61F 2/3662 623/23.26 |
| 5,376,123 A | * | 12/1994 | Klaue | A61B 17/8802 623/23.19 |
| 5,702,481 A | * | 12/1997 | Lin | A61F 2/3662 606/63 |
| 6,355,069 B1 | * | 3/2002 | DeCarlo, Jr. | A61F 2/3662 623/23.26 |
| 7,044,977 B2 | * | 5/2006 | Ferree | A61F 2/389 623/23.25 |
| 8,216,320 B2 | * | 7/2012 | Splieth | A61F 2/4684 623/22.45 |

(Continued)

*Primary Examiner* — Alvin J Stewart

(57) ABSTRACT

Expandable hip stem implants, systems, and methods of implanting a hip stem during a hip arthroplasty are provided. The implant may include a proximal body having a neck terminating at a free end, a distal stem having a proximal portion coupled to the proximal body and a distal portion, and a plurality of expandable bodies aligned around the distal stem. The plurality of expandable bodies have a collapsed configuration and an expanded configuration such that the plurality of expandable bodies expand radially outward away from one another.

10 Claims, 15 Drawing Sheets

(56) References Cited

U.S. PATENT DOCUMENTS

| | | | | |
|---|---|---|---|---|
| 8,409,295 | B2* | 4/2013 | Geller | A61F 2/3662 |
| | | | | 623/22.42 |
| 9,402,728 | B2* | 8/2016 | Liu | A61F 2/3676 |
| 9,486,318 | B2* | 11/2016 | Forsell | A61F 2/36 |
| 9,827,025 | B2* | 11/2017 | Jansen | A61B 17/7266 |
| 11,304,813 | B2* | 4/2022 | Peter | A61F 2/3601 |
| 2004/0019386 | A1* | 1/2004 | Ferree | A61F 2/442 |
| | | | | 623/23.22 |
| 2006/0004459 | A1* | 1/2006 | Hazebrouck | A61F 2/36 |
| | | | | 623/23.45 |
| 2008/0039950 | A1* | 2/2008 | Splieth | A61F 2/4684 |
| | | | | 623/23.26 |
| 2013/0018482 | A1* | 1/2013 | Meridew | A61F 2/30734 |
| | | | | 623/23.46 |
| 2013/0338780 | A1* | 12/2013 | Berchoux | A61F 2/4014 |
| | | | | 623/19.11 |
| 2014/0330390 | A1* | 11/2014 | Liu | A61F 2/3609 |
| | | | | 623/23.21 |

* cited by examiner

EXPANDABLE HIP STEM

FIELD OF THE INVENTION

The present application generally relates to hip arthroplasty and, in particular, to total hip arthroplasty implants.

BACKGROUND OF THE INVENTION

Hip arthroplasty, often called hip replacement, is a surgical procedure used to reconstruct and resurface a hip joint that has been damaged by disease or injury, such as by arthritis or hip fracture. Total hip arthroplasty (THA) devices may replace both the acetabulum and the femoral head which comprise the hip joint, where the femur articulates relative to the acetabulum. To replace the hip joint, the hip arthroplasty may include a femoral implant secured to the end of the femur and an acetabular implant secured to the acetabulum that forms a replacement articulating surface which interfaces with the femoral implant. The femoral implant is pivotably coupled to the acetabular implant, thereby reconstructing the hip joint.

During a total hip arthroplasty, a femoral neck osteotomy may be performed to remove the femoral head. Following this, a reamer may be used to locate the femoral canal and broach the bone until the cortical walls of the femur have been contacted. After a trial reduction is conducted to ensure the correct femoral head and neck offset is chosen, the stem of the implant is inserted into the broached canal and impacted. The femoral implant, after impaction, creates a press fit between the implant and the cortical walls of the femur. While femoral implant stems exist on the market, there is an opportunity to improve the fit of the stem within the prepared bone and thus reduce the potential for subsidence.

SUMMARY OF THE INVENTION

To meet this and other needs, implants, systems, and methods for installing a hip stem are provided. In particular, the hip stem may include an expandable hip stem configured to expand in the medial/lateral (ML), anterior/posterior (AP), and/or proximal/distal (PD) directions. The expandable hip stem may provide for a more custom fit based on the individual patient anatomy. The expandable stem may include a modular system, which may help to ease the difficulty of a revision hip, and also reduce inventory for size stems that are less commonly used in a primary total hip arthroplasty.

According to one embodiment, a system for hip arthroplasty includes a proximal body having a neck terminating at a free end and an expandable distal stem. The neck may be configured to support a femoral head component in articulating with the pelvis. The distal stem may be separated into one or more expandable sections including proximal medial, proximal lateral, distal medial, and/or distal lateral sections. One or more of these sections may be configured to expand medially, laterally, anteriorly, posteriorly, proximally, distally, or a combination thereof, thereby providing for an enhanced fit in the femoral canal.

According to another embodiment, a system for a hip arthroplasty includes a proximal body having a neck terminating at a free end, a distal stem having a proximal portion coupled to the proximal body and a distal portion, and a plurality of expandable bodies aligned around the distal stem. The plurality of expandable bodies have a collapsed configuration and an expanded configuration such that the plurality of expandable bodies expand radially outward away from one another.

The hip arthroplasty system may include one or more of the following features. Each expandable body may include a blade extending from a proximal end to a distal end. Each expandable body may include an inner surface with a concavity configured to contact an outer surface of the distal stem when the expandable bodies are in the collapsed configuration. The system may include a pair of opposed expandable bodies that form a cross-section of two semi-circles around the distal stem; a set of three expandable bodies such that a cross-section of three one-third circles encircle the distal stem; or a set of four expandable bodies such that a cross-section of four one-quarter circles enclose the distal stem. The distal stem may include a male tapered projection receivable in a tapered female opening in the proximal body, thereby coupling the distal stem to the proximal body. The plurality of expandable bodies may provide for expansion in the medial/lateral, anterior/posterior, and/or proximal/distal directions.

According to another embodiment, an implant for a hip arthroplasty includes a proximal body, a distal stem, a plurality of expandable bodies, and an actuation assembly. The proximal body has a neck terminating at a free end and a channel extending therethrough. The distal stem has a proximal portion coupled to the proximal body, a distal portion terminating at a conical end, and a channel extending through the distal stem aligned with the channel of the proximal body. The plurality of expandable bodies are positioned around the distal stem. Each expandable body has an inner surface facing toward the distal stem and an outer surface defining an outer diameter. The actuation assembly is configured for moving the plurality of expandable bodies. The plurality of expandable bodies have a collapsed configuration and an expanded configuration such that the plurality of expandable bodies expand radially outward away from one another, thereby enlarging the outer diameter.

The hip arthroplasty implant may include one or more of the following features. The actuation assembly may include a ramp body with one or more ramp surfaces configured to engage with one or more corresponding ramp surfaces along the inner surfaces of the expandable bodies. The ramp body may include a pair of opposed flat ramp surfaces or a single conical ramp. The actuation assembly may include a head portion and a threaded shaft that terminates at a distal end, and the threaded shaft may be receivable through the channel in the distal stem. Rotation of the threaded shaft translates a ramp body distally through the distal stem, thereby expanding the expandable bodies radially outward. The actuation assembly may include a plurality of extension springs aligned perpendicular to a longitudinal axis of the threaded shaft such that the extension springs are configured to pull the expandable bodies inward toward the distal stem.

According to another embodiment, an implant for a hip arthroplasty includes a proximal body, a distal stem, a plurality of expandable bodies, and an actuation assembly. The proximal body has a neck terminating at a free end and a channel extending therethrough. The distal stem has a proximal portion coupled to the proximal body, a distal portion terminating at a conical end, and a channel extending through the distal stem aligned coaxially with the channel of the proximal body. The plurality of expandable bodies are positioned around the distal stem. Each expandable body has an inner surface facing toward the distal stem and an outer surface. The actuation assembly includes a threaded shaft and a ramp body for moving the plurality of expandable bodies. Rotation of the threaded shaft translates the ramp body distally, thereby expanding the expandable bodies radially outward.

The hip arthroplasty implant may include one or more of the following features. The threaded shaft may include a head portion retained in the distal stem with an internal retaining ring, thereby ensuring the threaded shaft maintains its position within the distal stem while the ramp body translates. The ramp body may include a collar seated inside a recess in the channel in the distal stem and a pair of opposed flat ramp surfaces configured to engage with corresponding flat ramp surfaces along the inner surfaces of the expandable bodies. The threaded shaft may be positioned through the ramp body and terminates at a distal end connected to the conical end of the distal stem. The ramp body may include a single conical ramp positioned at a distal end of the threaded shaft configured to engage with corresponding ramp surfaces along the inner surfaces of the expandable bodies.

According to another embodiment, an implant for a hip arthroplasty includes a proximal body having a neck terminating at a free end, a distal stem, an angulating body, and an actuation assembly. The actuation assembly includes a threaded ramp shaft and a ramp body. When rotated, the threaded ramp shaft translates distally which, in turn, articulates the ramp body to push against a corresponding ramp on a medial side of the angulating body. The angulating body is configured to pivot laterally about a pivot pin, thereby providing angular expansion of the angulating body.

According to yet another embodiment, a method for a hip arthroplasty may include one or more of the following steps in any suitable order: (1) performing a femoral neck osteotomy to remove a femoral head of a femur; (2) inserting a reamer into a femoral canal and broaching the bone until cortical walls of the femur are contacted; (3) trialing a reduction to assess leg length and/or joint stability; (4) impacting a femoral implant with an expandable distal stem into the femoral canal; and (5) expanding the distal stem in the medial/lateral, anterior/posterior, and/or proximal/distal directions, thereby securing the distal stem in the femur with a more custom patient fit and increased fixation.

Also provided are kits including implants of varying types and sizes including femoral implant with expandable stems, modular implants and their components, instruments, and other components for performing the procedure.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein.

DETAILED DESCRIPTION OF THE INVENTION

Figure 1:
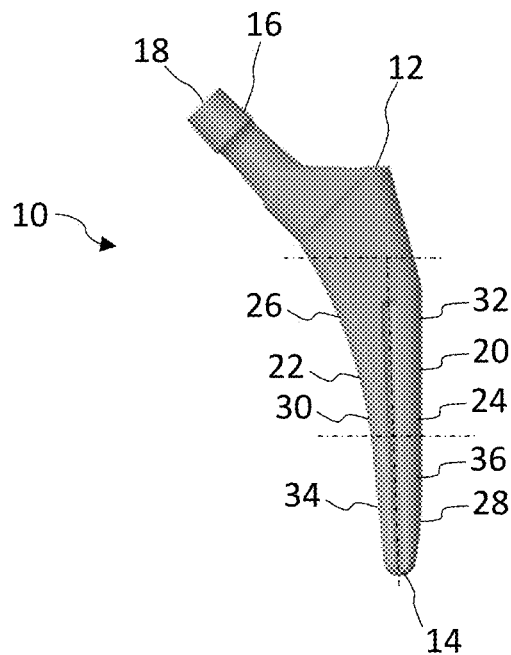
FIG. 1 shows a femoral implant including an expandable hip stem according to one embodiment.

Embodiments of the disclosure are generally directed to implants, systems, and methods for implanting hip stems, for example, during a hip arthroplasty. Specifically, embodiments are directed to expandable hip stems which may be configured to expand in the medial/lateral, anterior/posterior, and/or proximal/distal aspects, thereby improving the overall fit of the stem and minimizing the potential for subsidence.

During a total hip arthroplasty (THA), a femoral neck osteotomy may be performed to remove the femoral head after the correct size stem has been estimated, for example, in pre-operative templating. Following this, a reamer may be used to locate the femoral canal and broaching occurs until the cortical walls of the femur have been contacted. The broach sizes correlate to the size stems available. The surgeon utilizes the appropriate broach to choose the stem size more accurately. After a trial reduction is conducted to ensure the correct femoral head and neck offset is chosen, the stem is inserted into the broached canal and impacted. Trial reduction occurs with the broach left in the metaphysis. This may be used to assess leg length and joint stability. The implant, after impaction, creates a press fit against the implant and the cortical walls of the femur. An optional porous coating on the implant may allow for improved boney apposition to occur to provide further long-term fixation. The stems have numerous sizes which may vary in the medial/lateral, anterior/posterior, and/or proximal/distal aspects. These size variations allow for a wide range of patients to receive the size stem most appropriate to their anatomy. These stems may also come in a standard and lateralized neck offset. A surgeon may utilize a lateralized stem to further balance the ligaments within the joint while conducting trial reduction and range of motion (ROM). There is opportunity to improve the fit of the stem with respect to the prepared bone and thus reduce the potential for subsidence.

A revision total hip arthroplasty may be conducted for reasons like, but not limited to, degradation/reduction of bone quality and/or loosening, dislocation, or failure of the implant (either femoral stem or acetabular system). In a revision total hip arthroplasty, the existing stem is removed and any appropriate alterations (resections, burring, reaming, broaching, etc.) are made to prepare the femur for a new stem different from that of a primary total hip arthroplasty. The new stem implanted, whether cemented or cementless, must fixate into an altered broached cavity. Depending on patient anatomy/bone quality, stem fixation in a revision setting may be more difficult to achieve as opposed to a primary total hip arthroplasty. Revision stems also vary and may include solid core stems and modular systems that utilize variable proximal bodies and a distal stem in tandem to further achieve appropriate proximal/distal fixation.

As described herein, expandable hip stems may be configured to expand in the medial/lateral, anterior/posterior, and/or proximal/distal aspects to offer a more custom fit based off of individual patient anatomy. The expandable design may also include a modular system, which may help to ease the difficulty of a revision hip, and also reduce inventory for size stems that are less commonly used in a primary total hip arthroplasty.

Although embodiments are generally described with reference to a hip arthroplasty, it will be appreciated that the implants and systems described herein may be applied to other orthopedic locations and applications, such as the spine including between vertebrae, joints such as the knee, elbow, or shoulder, long bones such as a tibia, a humerus, a clavicle, a fibula, an ulna, a radius, bones of the foot, bones of the hand, or other suitable bone(s) or joints.

The implants and components thereof may be comprised of one or more biocompatible materials. For example, the implant may be made from a metal, such as titanium, stainless steel, cobalt chrome, carbon composite, or suitable alloys, a plastic or polymer, such as polyethylene, ultra-high molecular weight polyethylene (UHMWPE), polyetheretherketone (PEEK), or combinations of such materials. These parts may be machined, constructed from additive manufacturing, such as 3D printing, subtractive manufacturing, or hybrid manufacturing processes. Although the materials described herein are exemplified, it will be appreciated that any suitable materials and construction may be selected for the individual components.

Additional aspects, advantages and/or other features of example embodiments of the invention will become apparent in view of the following detailed description. It should be apparent to those skilled in the art that the described embodiments provided herein are merely exemplary and illustrative and not limiting. Numerous embodiments and modifications thereof are contemplated as falling within the scope of this disclosure and equivalents thereto.

Referring now to FIGS. 1-7C, embodiments of expandable hip stem implants 10 are shown. The types of expansions that may be applicable in an expandable hip stem 10 may include expansion in the medial/lateral, anterior/posterior, and/or proximal/distal aspects. The expansion(s) may also occur as a combination of multiple expansion types.

With further emphasis on FIG. 1, the expandable hip stem implant 10 is a femoral implant configured to be inserted into the femoral canal of a proximal femur. The expandable hip stem implant 10 includes a proximal end 12 and a distal end 14 with a longitudinal axis therebetween. A neck 16 extends at an angle from the proximal end 12 of the stem 10. The neck 16 terminates at a free end 18 configured to support a femoral head component (not shown) in articulating with the pelvis. The femoral head may be generally spherical, with a spherical outer surface. The femoral head defines a cavity sized and shaped to receive the neck 16 of the femoral implant 10 to couple the femoral head to the femoral implant 10. Although implant 10 depicts a lateral neck offset, it will be appreciated that all concepts are applicable to standard neck offsets as well.

The implant 10 includes a shank or distal stem 20 configured to expand in one or more sections. The shank 20 includes a medial side 22 and a lateral side 24. The distal stem 20 may be divided into a proximal portion 26 and a distal portion 28. As illustrated by the dashed lines in FIG. 1, the distal stem 20 may be separated into one or more expandable sections: proximal medial 30, proximal lateral 32, distal medial 34, and/or distal lateral 36. The dashed lines are exemplary and the expandable sections could be of different lengths, widths, or areas as determined for optimal expansion and desired patient fit. It will further be appreciated that in this embodiment the neck 16 is offset to the left but could be reversed for an offset to the right, which would reverse the medial and lateral sides 22, 24 of the implant 10 such that the implant 10 is configured to fit both anatomical hips of the patient. The orientation of the sections could also be modified to provide for expansion in the anterior/posterior directions, for example.

Figure 2A:
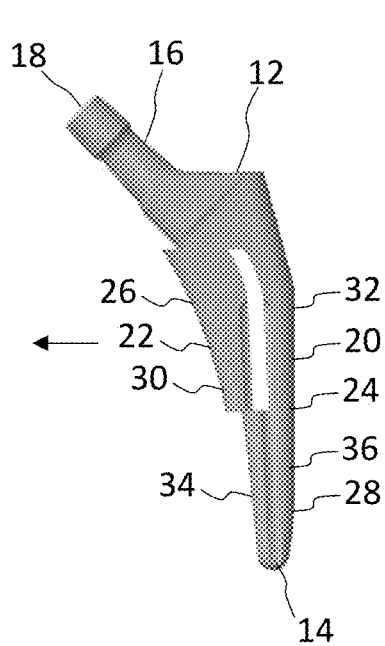
FIGS. 2A-2B show femoral implants configured to expand in the proximal medial direction and the distal medial direction, respectively.
Figure 2B:
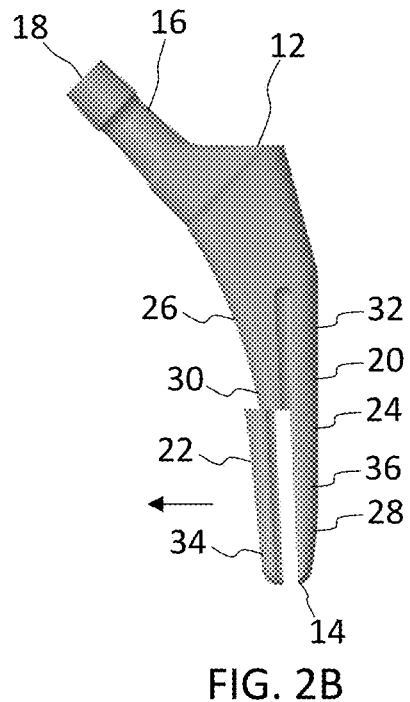
Figure 3A:
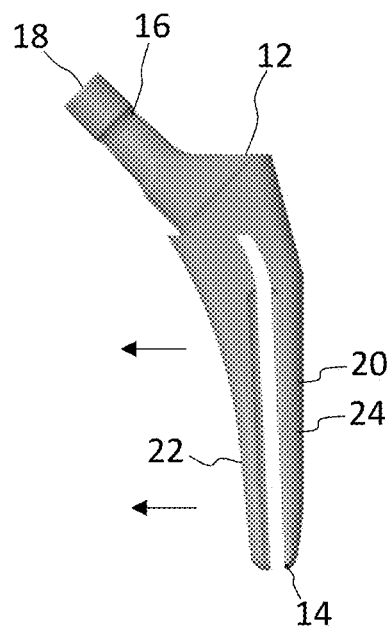
FIG. 3A-3C show femoral implants configured to expand in the full medial direction, with extended expansion in the proximal medial direction, and with extended expansion in the distal medial direction, respectively.
Figure 3B:
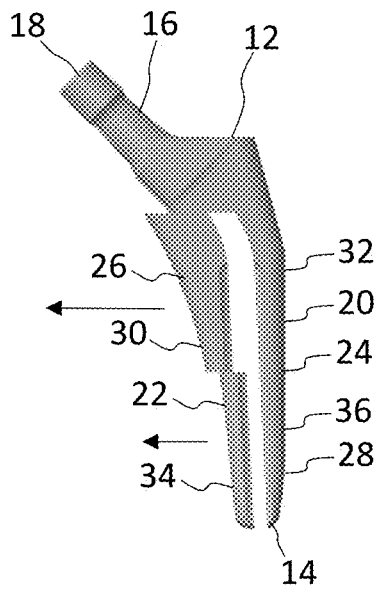
Figure 3C:
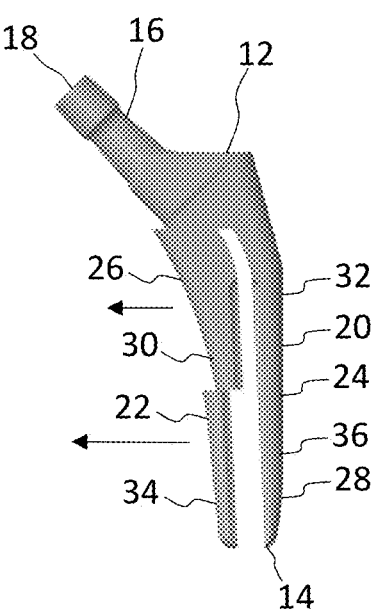

Turning now to FIGS. 2A-3C, alternative types of expansion in the medial direction are shown. FIG. 2A depicts expansion of only the proximal medial section 30 toward the medial direction, which creates a gap between the proximal sections 30, 32 of the stem 20. The distal sections 34, 36 remain unexpanded. FIG. 2B shows expansion of only the distal medial section 34 in the medial direction, which creates a gap between the distal sections 34, 36 of the stem 20. The proximal sections 30, 32 remain unexpanded. FIG. 3A shows full medial expansion such that the entire medial side 22 expands away from the lateral side 24, thereby creating a full length gap therebetween. FIG. 3B depicts full medial expansion of the proximal medial and distal medial sections 30, 34 with extended expansion of the proximal medial section 30. As shown, the gap between the proximal sections 30, 32 is greater in width than the gap between the distal sections 34, 36. FIG. 3C shows full medial expansion of the proximal medial and distal medial sections 30, 34 with extended expansions of the distal medial section 34. In this version, the gap between the distal sections 34, 36 is greater in width than the gap between the proximal sections 30, 32. Although variations of medial expansion are shown, it will be appreciated that the type, degree, and amount of expansion may be selected based on surgeon preference and patient anatomy.

Figure 4A:
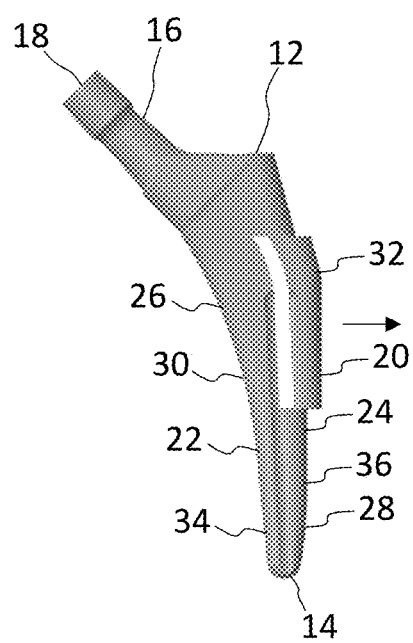
FIGS. 4A-4B show femoral implants configured to expand in the proximal lateral direction and distal lateral direction, respectively.
Figure 4B:
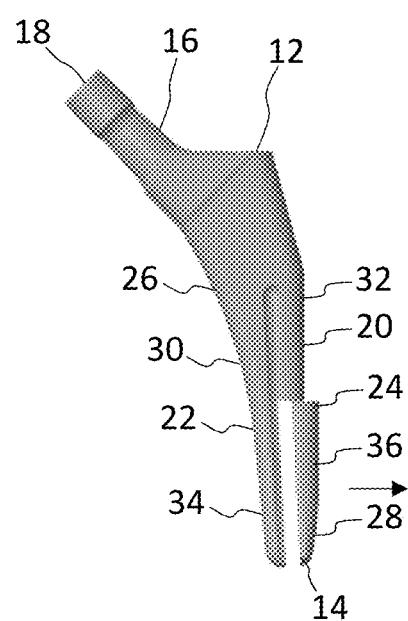
Figure 5A:
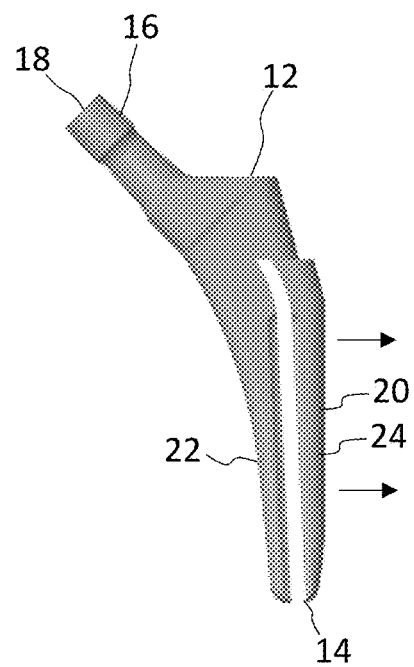
FIGS. 5A-5C show femoral implants configured to expand in the full lateral direction, with extended expansion in the proximal lateral direction, and with extended expansion in the distal lateral direction, respectively.
Figure 5B:
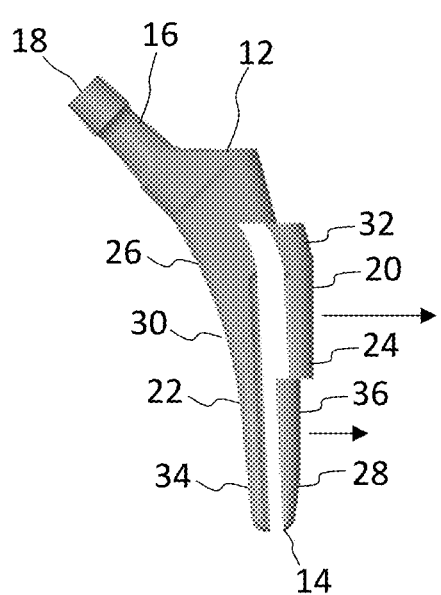
Figure 5C:
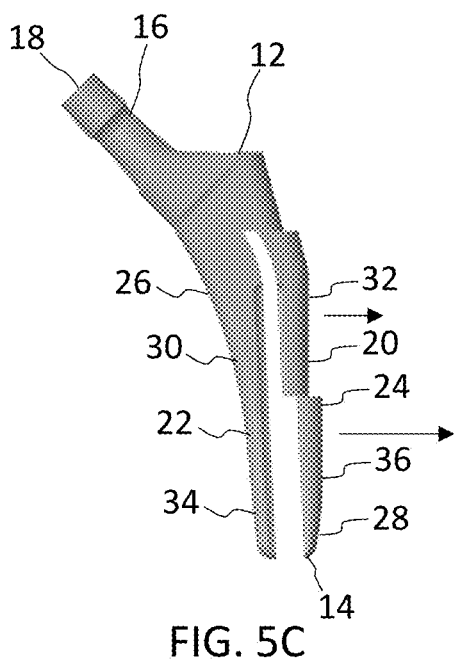

Turning now to FIGS. 4A-5C, alternative types of expansion in the lateral direction are shown. FIG. 4A depicts expansion of only the proximal lateral section 32 toward the lateral direction, which creates a gap between the proximal sections 30, 32 of the stem 20. The distal sections 34, 36 remain unexpanded. FIG. 4B shows expansion of only the distal lateral section 36 in the lateral direction, which creates a gap between the distal sections 34, 36 of the stem 20. The proximal sections 30, 32 remain unexpanded. FIG. 5A shows full lateral expansion such that the entire lateral side 24 expands away from the medial side 22, thereby creating a full length gap therebetween. FIG. 5B depicts full lateral expansion of the proximal lateral and distal lateral sections 32, 36 with extended expansion of the proximal lateral section 32. As shown, the gap between the proximal sections 30, 32 is greater in width than the gap between the distal sections 34, 36. FIG. 5C shows full lateral expansion of the proximal lateral and distal lateral sections 32, 36 with extended expansions of the distal lateral section 36. In this version, the gap between the distal sections 34, 36 is greater in width than the gap between the proximal sections 30, 32. Although variations of lateral expansion are shown, it will be appreciated that the type, degree, and amount of expansion may be selected based on surgeon preference and patient anatomy.

Figure 6A:
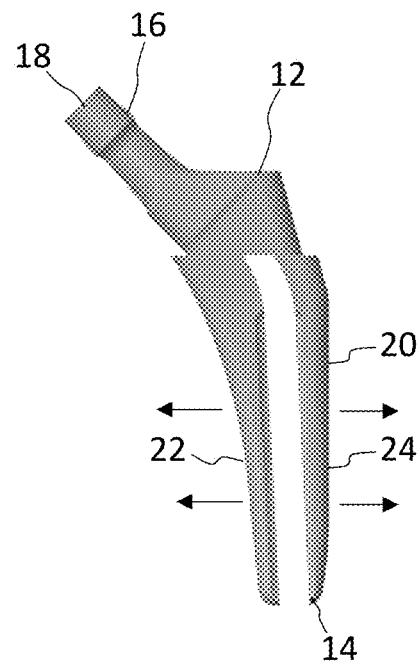
FIGS. 6A-6C show femoral implants configured to expand in the full medial and lateral directions, with extended expansion in the proximal medial and lateral directions, and with extended expansion in the distal medial and lateral directions, respectively.
Figure 6B:
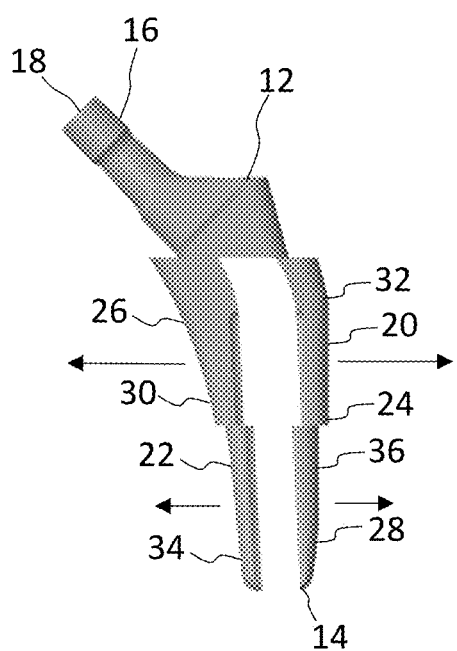
Figure 6C:
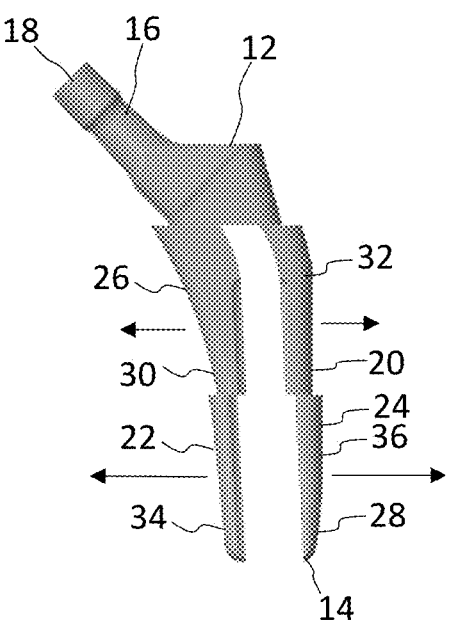

Turning now to FIGS. 6A-6C, variations of medial and lateral expansion are shown. FIG. 6A shows full medial and lateral expansion such that the entire medial side 22 and entire lateral side 24 of the stem 20 expand away from one another, thereby creating a full length gap therebetween. FIG. 6B depicts full medial and lateral expansion between the medial sections 30, 34 and the lateral sections 32, 36 with extended expansion of the proximal medial and lateral sections 30, 32. As shown, the gap between the proximal sections 30, 32 is greater in width than the gap between the distal sections 34, 36. FIG. 6C shows full medial and lateral expansion between the medial sections 30, 34 and the lateral sections 32, 36 with extended expansions of the distal medial and lateral sections 34, 36. In this version, the gap between the distal sections 34, 36 is greater in width than the gap between the proximal sections 30, 32. Although variations of medial and lateral expansion are shown, it will be appreciated that the type, degree, and amount of expansion may be selected based on surgeon preference and patient anatomy.

Figure 7A:
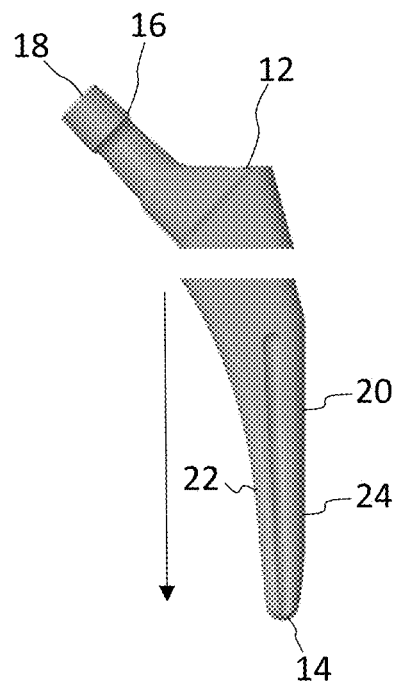
FIGS. 7A-7C show femoral implants configured to expand in the upper distal direction, the lower distal direction, and with full distal expansion in the upper and lower distal portions, respectively.
Figure 7B:
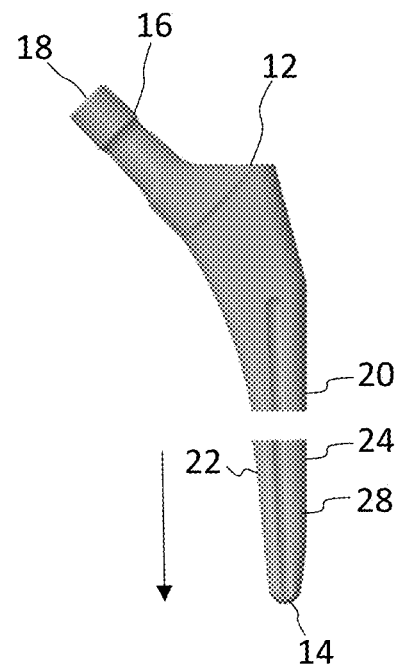
Figure 7C:
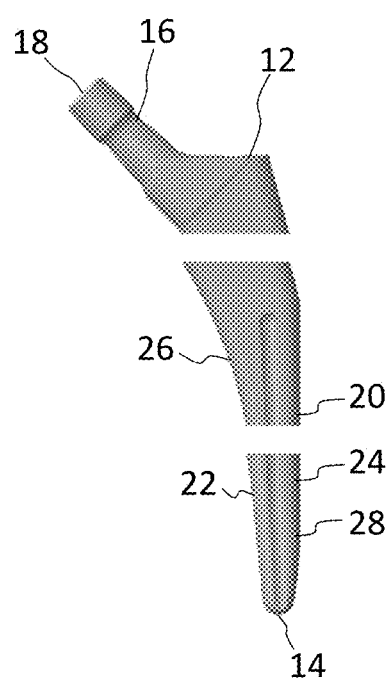

Turning now to FIGS. 7A-7C, variations of distal expansion are shown. FIG. 7A shows expansion of the entire upper distal section. As shown, a gap between the proximal end 12 and distal stem 20 may be increased to increase the overall length of the implant 10. FIG. 7B shows expansion of the lower distal section 28. Similarly, a gap in the stem 20 (e.g., about midway) may be increased to increase the overall length of the implant 10. FIG. 7C shows full distal expansion of the proximal portion 26 and distal portion 28 of the stem 20. A pair of gaps (or more) may each be increased to increase the overall length of the implant 10. Although variations of distal expansion are shown, it will be appreciated that the type, degree, and amount of expansion may be selected based on surgeon preference and patient anatomy.

Figure 8A:
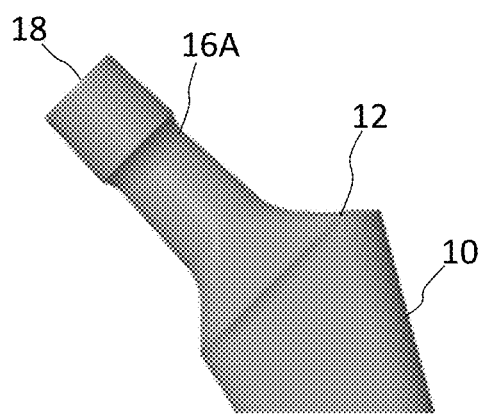
FIGS. 8A-8B show the proximal body of the femoral head with a neck offset and lateralized neck offset, respectively.
Figure 8B:
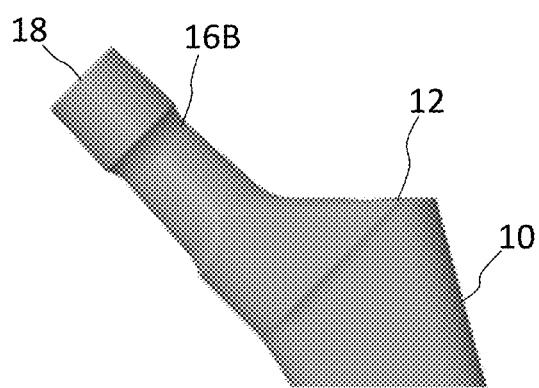

FIGS. 8A-8B show variations of neck offsets. FIG. 8A depicts a standard neck offset 16A and FIG. 8B shows a lateralized neck offset 16B. Surgeons may utilize a lateralized stem, for example, to decrease laxity in the joint. With the use of medial and/or lateral expansion, the surgeon may desire to increase or decrease laxity as needed since the stem 20 may be configured to translate in the medial/lateral aspect similar to the neck offsets 16.

Figure 9A:
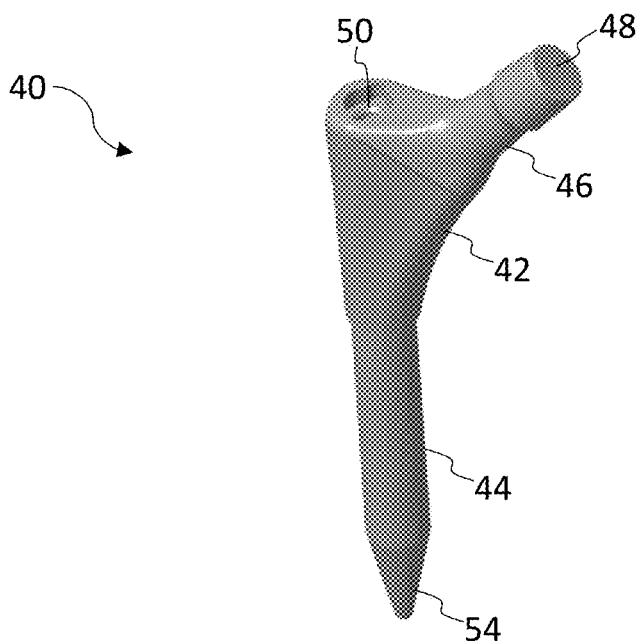
FIGS. 9A-9C shows an assembled modular stem, the proximal body of the modular stem, and the distal stem of the modular stem, respectively.
Figure 9B:
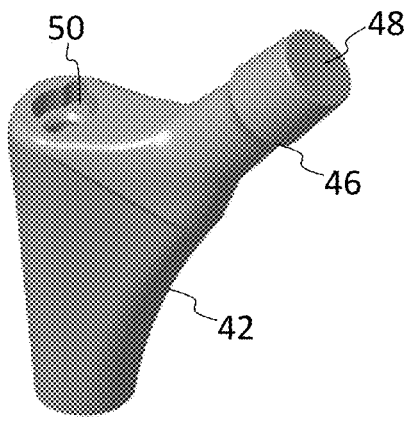
Figure 9C:
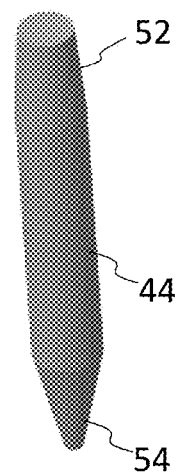

FIGS. 9A-9C depict a modular stem system 40 according to one embodiment. The modular system 40 may include a proximal body 42 and a distal stem 44 which attaches to the proximal body 42. Similar to implant 10, the proximal body 42 includes a neck 46 that terminates at free end 48 to which the femoral head (not shown) attaches. The proximal body 42 defines a through channel 50 for receiving an instrument. The stem 44 may include a morse taper 52 receivable in an opening 56 in the distal end of the proximal body 42. Although a morse taper 52 is exemplified, any suitable connection may be used between the distal stem 44 and the proximal body 42 to join the modular components together. The opposite end 54 of the stem 44 may form a conical end, a pointed section, or may be otherwise configured to be inserted into bone. The two-part stem system 40 may be useful to better accommodate a revision surgery. Once fully assembled and implanted, stem implant 40 functions nearly identically to that of a solid core stem. The two-part system 40 may contain various designs of proximal bodies 42 and distal stems 44 that may offer enhanced anterior/posterior, medial/lateral, and proximal/distal fixation on a per patient basis.

Figure 10A:
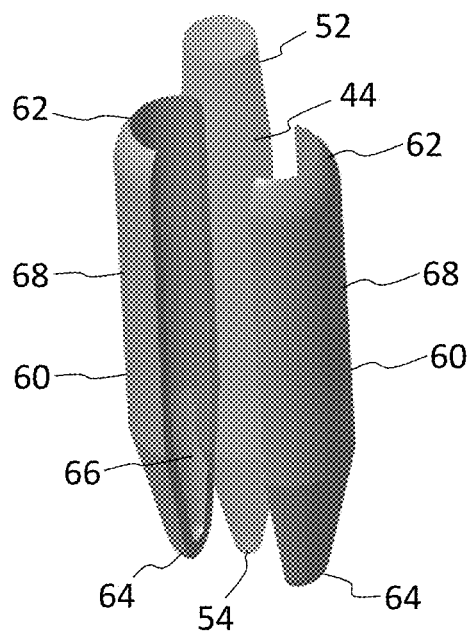
FIGS. 10A-10C show radial expansion of the distal stem including a pair, triple, and quad, respectively, of expanding bodies about the distal stem of the implant.
Figure 10B:
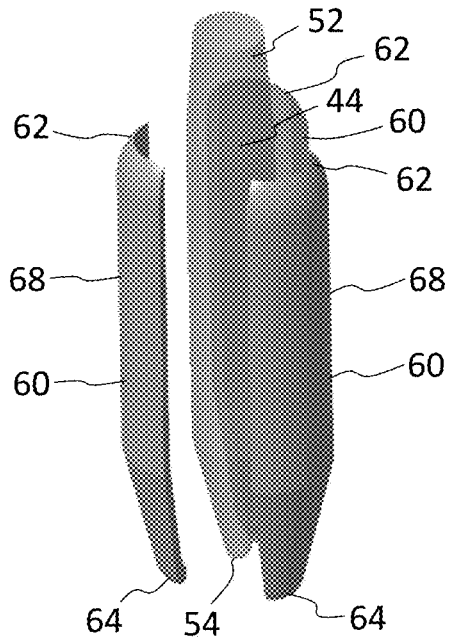
Figure 10C:
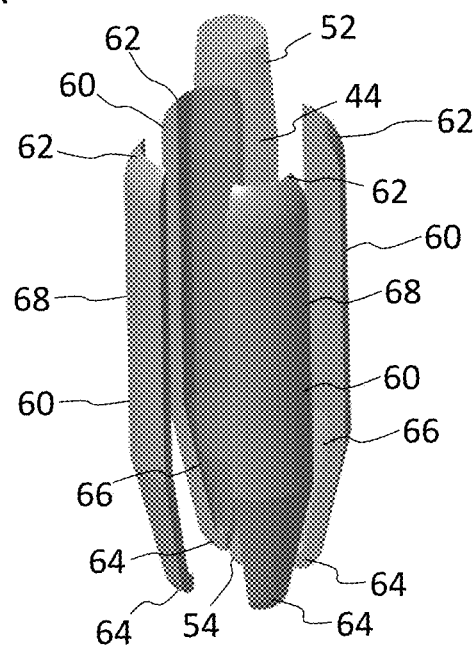

Turning now to FIGS. 10A-10C, examples of radial expansion of the distal stem 44 are shown. In one embodiment, a plurality of expandable bodies 60 may be aligned around the distal stem 44, thereby encircling the stem 44. The expandable bodies 60 may be configured to generally mimic the outer shape of the distal stem 44. Each expandable body 60 may include a blade or elongate body extending from a proximal end 62 to a distal end 64. Each blade 60 may be flat, angled, curved, or otherwise configured to fit inside the bone. The proximal end 62 of each expandable body 60 may be generally aligned with or near the tapered end 52 of the stem 44 and the distal end 64 of the expandable body 60 may be generally aligned with or near pointed end 54 of the stem 44. The distal ends 64 of the expandable bodies 60 may be tapered or generally conical to mimic the taper or conical shape of stem end 54 when collapsed about the stem 44.

Each expandable body 60 may include an inner surface 66 facing toward the distal stem 44 and an opposite outer surface 68. The inner surface 66 may define a cavity or concavity configured to contact the outer surface of the stem 44 when the expandable bodies 60 are in a collapsed position. The expandable bodies 60 are configured to expand radially outward thereby increasing the footprint of the distal stem 44. When expanded radially outward, the expandable bodies 60 move away from one another and enlarge the overall outer diameter of the distal stem 44, thereby securing the stem 44 in the bone.

Depending on the quantity and orientation, the expanding bodies 60 may provide for expansion in the medial/lateral, anterior/posterior, and/or proximal/distal aspects. The radial expansion may also allow for a combination of multiple expansion types. FIG. 10A depicts a double set or pair of opposable expandable bodies 60, which generally form a cross-section of two semi-circles around the stem 44. Double expansion may be situated in the medial/lateral aspect for more distal fixation. FIG. 10B depicts a triple set of expandable bodies 60 such that three one-third circles encircle the stem 44. FIG. 10C shows a quad set of expandable bodies 60 such that a cross-section of four one-quarter circles enclose the stem 44. The triple and quad iterations of expansion may offer a more equal dispersion of stress that is enacted on the stem during patient use. The triple and quad bodies 60 may also enhance the fit of the stem per patient and greatly increase fixation in the anterior/posterior and/or medial/lateral aspects. It will be appreciated that any suitable number, position, and shape of expandable bodies 60 may be selected to achieve the desired expansion of the stem 44. In the embodiments shown, alternative types of expansion are provided about the distal stem 44 of the two-part stem 40, although it will be appreciated that the expandable bodies 60 may also be provided about a solid core stem 10 or other suitable implant.

Any of the implants described herein or a portion thereof may include one or more coatings, such as porous, plasma-sprayed, grit blasted, or other surface enhancements configured to promote bony ingrowth for long term fixation. For example, a porous coating may be applied to the proximal portion of the stem to allow for improved boney apposition to occur and encourage greater fixation in the metaphysis. The stems may include features such as fluted ridges, tapered geometry, and/or grit blasting to further increase boney apposition, fixation, and/or load dispersion. The expanding bodies of the distal stem may also exhibit one or more of the surface enhancement features mentioned herein to further offer a more custom patient fit and increase fixation.

Figure 11A:
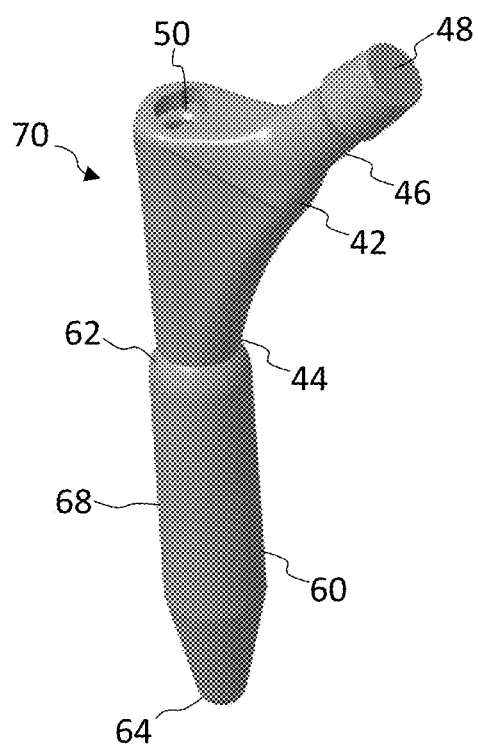
FIGS. 11A-11B shows the modular femoral implant with the expanding bodies contracted into the distal stem and radially expanded outward about the distal stem, respectively.
Figure 11B:
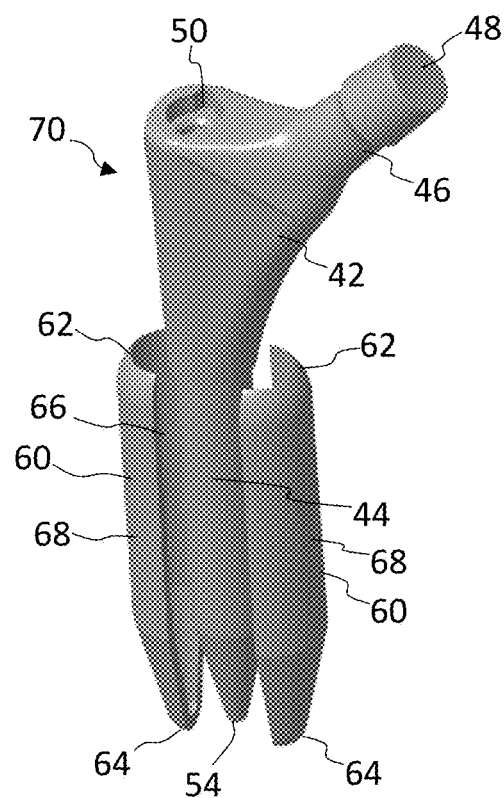

FIGS. 11A-11B show an embodiment of modular implant 70 similar to modular implant 40 with two opposable expandable bodies 60 configured for expanding the distal stem 44. As shown, the modular implant 70 is fully assembled with the morse taper 52 inserted into the end 56 of the proximal body 42. FIG. 11A shows the implant 70 in the initial insertion configuration with the expandable bodies 60 fully collapsed about the stem 44. FIG. 11B shows the implant 70 in the expanded configuration with the expandable bodies 60 radially expanded outward and away from one another.

Figure 12:
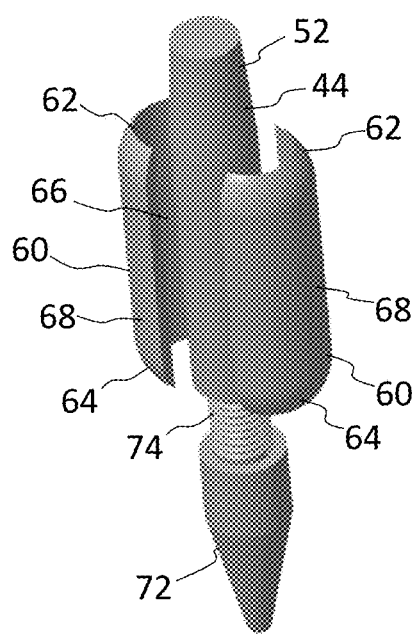
FIG. 12 shows the femoral implant with a pair of expanding bodies and an interchangeable distal tip according to one embodiment.

FIG. 12 depicts a distal stem 44 with a removable tip 72. In this embodiment, the modular implant 70 allows for radial expansion and also allows for customization of the tip 72 that may be utilized with the stem 44. The removable tip 72 may be connected with an attachment member 74, which connects the tip 72 to the distal end of the stem 44. The attachment member 74 may include a threaded shaft, a press-fit connection, or other suitable fitting to couple the tip 72 to the distal stem 44. The attachment member 74 may also allow for movement of the tip 72 such that a distal or proximal adjustment in length may be achieved. Further, the interchangeable tips 72 may vary in size in the proximal/distal aspect to allow for the stem 44 to achieve fixation past the metaphysis and deeper into the diaphysis of the femur. These tips 72 may vary as follows: pointed (as shown), rounded, or slotted (thigh pain reduction). The coating/geometry of these tips 72 may be customized similar to that of the stem 44 and/or expandable bodies 60, such as porous coating, fluted ridges, continuation of tapered geometry, grit blasted, or other suitable surface enhancements.

Figure 13A:
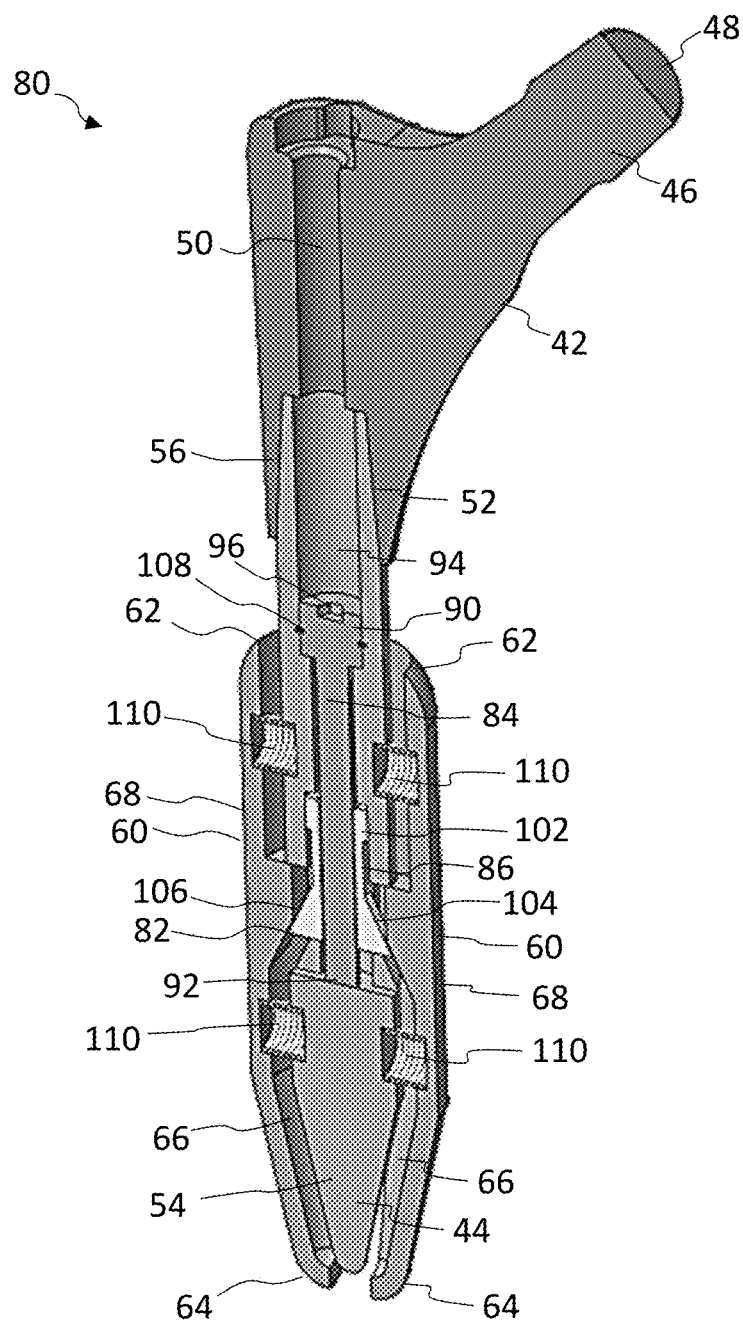
FIGS. 13A-13B show a cross-sectional view and a transparent isometric view, respectively, of an expandable hip stem with a self-retaining flat ramp according to one embodiment.
Figure 13B:
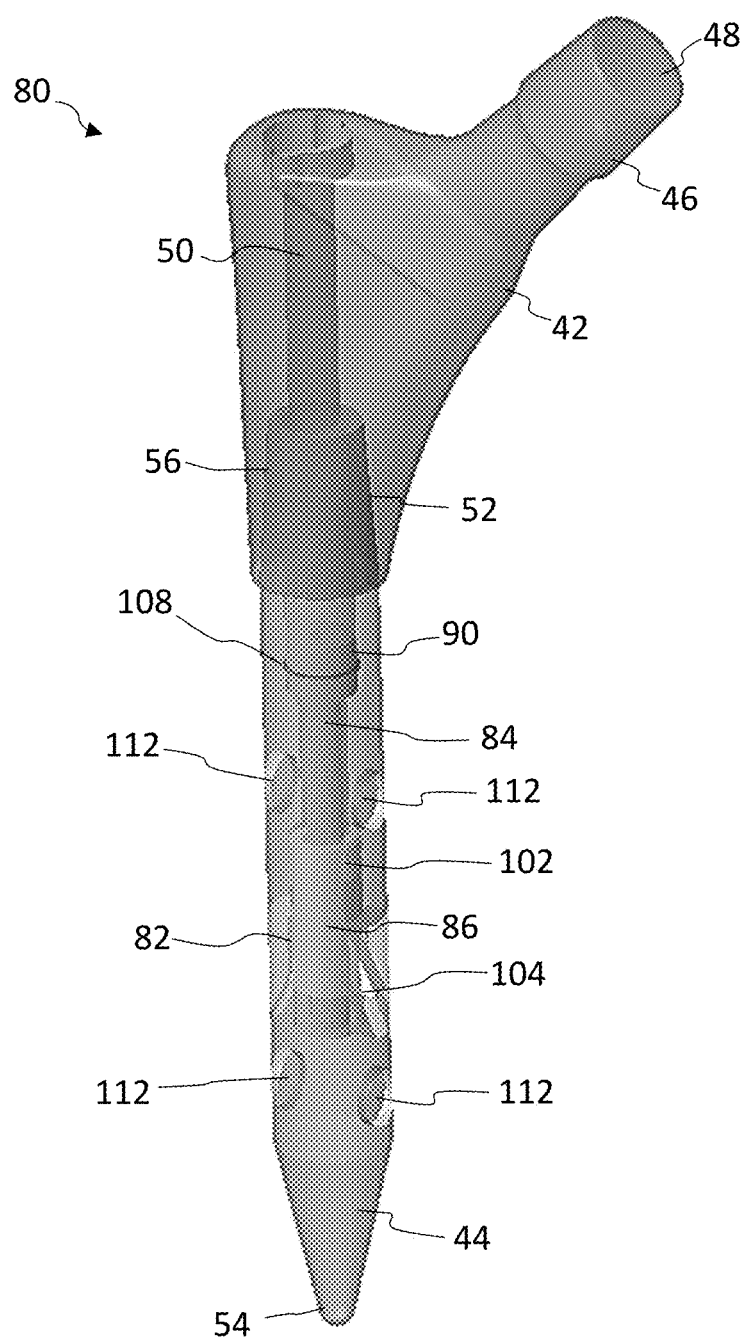

Turning now to FIGS. 13A-13B, an embodiment of modular implant 80 is shown similar to modular implant 70 with two opposable expandable bodies 60 configured for radially expanding the distal stem 44. FIG. 13A shows an isometric cross-sectional view of the modular implant 80 and FIG. 13B shows a transparent isometric view omitting the expanding bodies 60 and springs 110 for clarity. In this embodiment, the two-part stem system 80 includes proximal body 42, distal stem 44, and two expanding bodies 60 configured for radial expansion.

The proximal body 42 may be attached to the distal stem 44 with a tapered interface 52, 56, such as a morse taper. The proximal body 42 defines female tapered opening 56 at the distal end sized and configured to receive the male tapered projection 52 of the stem 44. When the proximal body 42 is impacted onto the distal stem 44, the two tapered surfaces 52, 56 engage and lock the bodies 42, 44 together due to a cold weld that occurs between the tapered surfaces 52, 56, similar to that of the femoral head and neck fit. It will be appreciated that the interface may be reversed or any suitable connection between the proximal body 42 and distal stem 44 may be selected to secure the modular parts together.

The expandable bodies 60 are configured to expand via a translation actuation assembly 82. Translation assembly 82 may include a threaded shaft 84 and a ramp body 86. The threaded shaft 84 may include a head portion 90 and the shaft 84 may terminate at distal end 92, which is affixed to the distal portion 54 of the distal stem 44. The shaft 84 may be threaded along its length with one or more external threads configured to mate with corresponding internal threads in the ramp body 86. The head portion 90 may be receivable inside a channel 94 through the tapered portion 52 of the distal stem 44. The channel 94 may be coaxially aligned with the channel 50 through the proximal body 42 along a longitudinal axis. An instrument recess 96 may be provided at the top of the shaft 84 in the head portion 90. An instrument (not shown) may be inserted into the channel 50, through channel 94, and engaged with recess 96 in the threaded shaft 84 in order to rotate the threaded shaft 84 and enact expansion of the expandable bodies 60. The instrument recess 96 may be a hex recess or other instrument recess to suit any instrument that may be utilized in rotating the shaft 84.

The threaded shaft 84 may be positioned through and engaged with ramp body 86. Ramp body 86 may include a collar 102 and one or more ramp surfaces 104. The collar 102 may be seated inside a recess within channel 94 through the stem 44. The one or more ramp surfaces 104 of the ramp body 86 are configured to engage with one or more corresponding ramp surfaces 106 along the inner surfaces 66 of the expandable bodies 60. The ramp surfaces 104, 106 may include flat, curved, beveled, or other suitable mating surfaces configured to expand the expandable bodies 60. In one embodiment, the ramp body 86 is a self-retaining flat ramp with multiple flat ramps (e.g., a pair of opposed ramps 104) configured to engage with each of the expandable bodies 60. The opposed ramps 104 may widen away from one another as the ramps 104 extend distally.

When the threaded shaft 84 rotates clockwise or counter-clockwise, the ramp body 86 translates in the proximal or distal aspect, respectively. The ramps 104 on the ramp body 86 contact the corresponding ramps 106 on the expanding bodies 60 and create translation in the medial/lateral or anterior/posterior aspect, depending on how the surgeon situates the radial stem within the intramedullary cavity. Although the assembly 82 is shown for double expandable bodies 60, it will be appreciated that similar expansion can occur for triple, quad, or other iterations.

The assembly 82 may further include an internal retaining ring 108 connecting the head 90 of the shaft 84 to the body of the stem 44. The internal retaining ring 108 ensures the threaded shaft 84 maintains its position within the stem 44 while the ramp body 86 translates along the proximal/distal aspect. The assembly 82 may also include one or more extension springs 110. The extension springs 110 may be aligned generally transverse, such as perpendicular to the longitudinal axis of the shaft 84. The springs 110 may be receivable through channels 112 in the distal stem 44 and into inner surfaces 66 in the expandable bodies 60. For example, two extensions springs 110 may be provided near the proximal ends 62 of the expandable bodies 60 and two extension springs 110 may be provided near the distal ends 64 of the expandable bodies 60. Two extension springs 110 may be positioned above the ramp body 86 and two extension springs 110 may be positioned below the ramp body 86. The extension springs 110 allow for the assembly 82 to be self-retaining and offers support when the stem 44 is actively expanding to prevent angulation of the expanding bodies 60. In the case that a surgeon must remove the stem 80 in the initial surgery or in future surgeries, these extension springs 110 pull the expanding bodies 60 inward toward the stem 44 and allow for easier extraction.

Figure 14A:
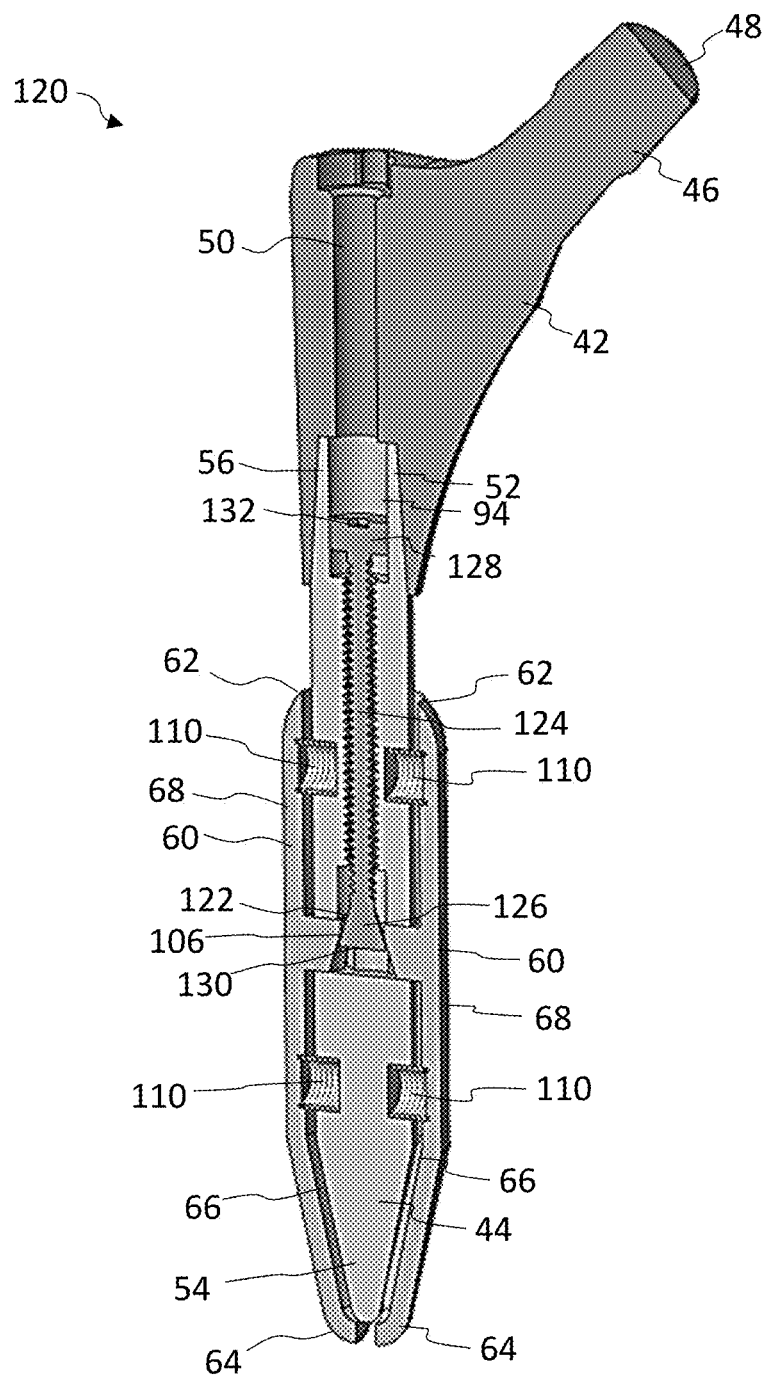
FIGS. 14A-14B show a cross-sectional view and a transparent isometric view, respectively, of an expandable hip stem with a self-retaining conical ramp according to one embodiment.
Figure 14B:
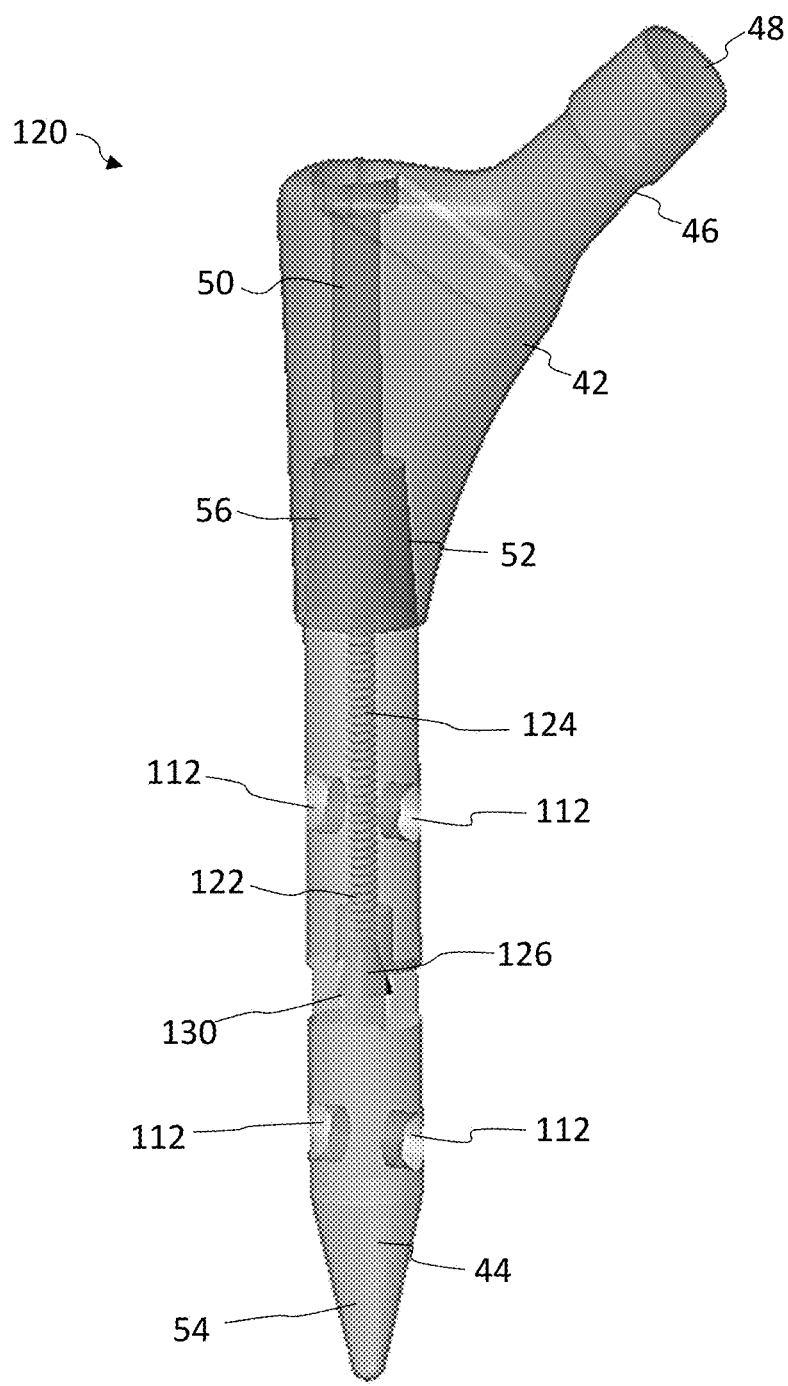

Turning now to FIGS. 14A-14B, an embodiment of modular implant 120 is shown similar to modular implant 80 with two opposable expandable bodies 60 configured for expanding the distal stem 44 with a singular conical ramp 126 as opposed to multiple flat ramps 104. FIG. 14A shows an isometric cross-sectional view of the modular implant 120 and FIG. 14B shows a transparent isometric view omitting the expanding bodies 60 and springs 110 for clarity. In this embodiment, the expansion assembly 122 includes a threaded shaft 124 with a singular conical ramp body 126 at its distal end 130, which engages with the ramped surfaces 106 inside the expandable bodies 60 to thereby radially expand the expandable bodies 60 outward. The threaded conical ramp shaft 124 combines the ramp body 126 and threaded shaft 124 into a single part. When the self-retaining conical ramp shaft 124 is rotated, the shaft 124 translates along the proximal/distal aspect allowing for the conical ramp 126 to push against the corresponding ramps 106 on the expanding bodies 60, thereby creating expansion.

Similar to implant 80, the proximal body 42 may be attached to the distal stem 44 using a morse taper interface 52, 56. When the proximal body 42 is impacted onto the distal stem 44, the two tapered surfaces 52, 56 engage and lock the bodies 42, 44 together. It will be appreciated that any suitable connection between the proximal body 42 and distal stem 44 may be selected to secure the parts together.

The expandable bodies 60 are configured to expand via expansion actuation assembly 122. Expansion assembly 122 may include threaded shaft 124 with conical ramp body 126. The threaded shaft 124 may include a head portion 128 and the shaft 122 may terminate at distal end 130, which is integral with the conical ramp body 126. The head portion 128 may be receivable inside channel 94 through the tapered male portion 52 of the distal stem 44. An instrument recess 132 may be provided at the top of the shaft 124 in the head portion 128. An instrument (not shown) may be inserted into the channel 50, through channel 94, and engaged with recess 132 in the threaded shaft 124, thereby rotating the threaded shaft 124 and enacting expansion.

The distal end 130 of the threaded shaft 124 includes conical ramp body 126 with a single conical ramp configured to engage with one or more corresponding ramp surfaces 106 along the inner surfaces 66 of the expandable bodies 60. As the threaded shaft 124 rotates clockwise or counterclockwise, the conical ramp body 126 translates in the proximal/distal aspect, respectively. The conical ramp body 126 contacts the corresponding ramps 106 on the expanding bodies 60 and creates translation in the medial/lateral or anterior/posterior aspect, depending on how the surgeon situates the radial stem within the intramedullary cavity. Although the assembly 122 is shown for double expandable bodies 60, it will be appreciated that similar expansion can occur for triple, quad, or other configurations.

Similar to implant 80, the assembly 122 may also include one or more extension springs 110, which allow for the assembly 122 to be self-retaining and offer support when the stem 44 is actively expanding to prevent angulation of the expanding bodies 60. In the case of stem removal during the initial surgery or in a subsequent surgery, with the ramp body 126 retracted, the extension springs 110 are configured to pull the expanding bodies 60 inward toward the stem 44 and allow for easier extraction.

Figures 15A, 15B:
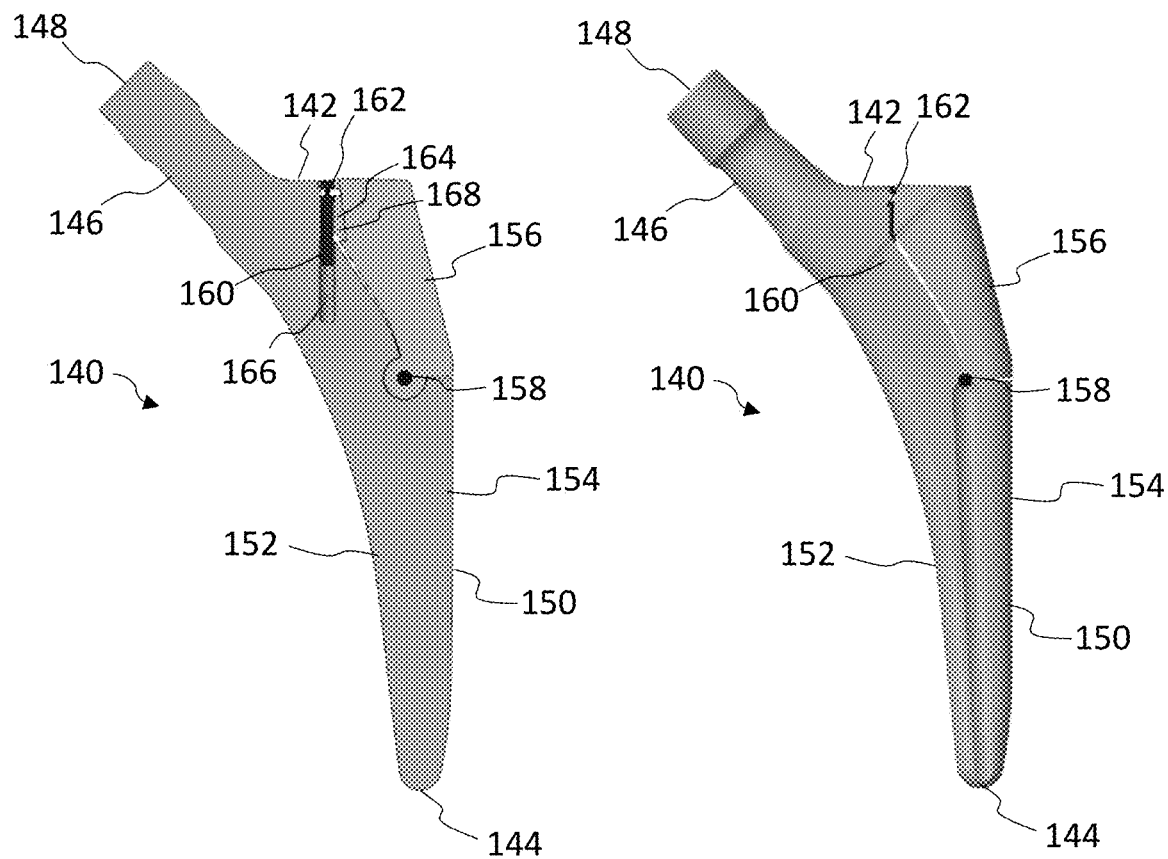
FIGS. 15A-15C show cross-sectional, anterior-posterior, and transparent isometric views, respectively, of the femoral head implant with an angulating body configured to fill the proximal metaphasis of the femur.
Figure 15C:
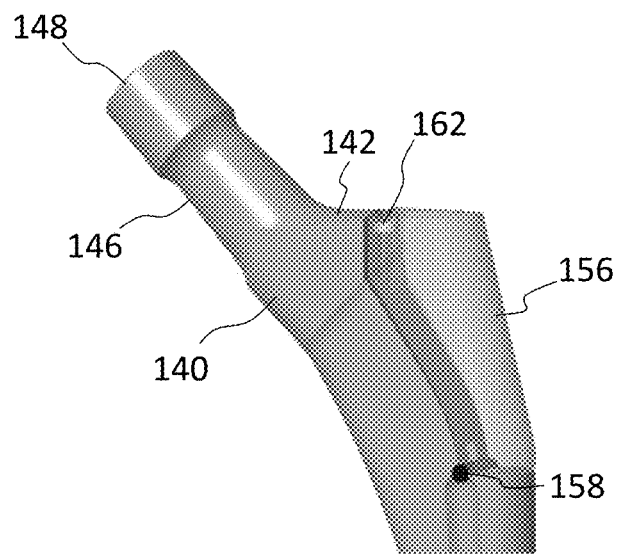

Turning now to FIGS. 15A-15C, one embodiment of an angulating hip stem 140 is shown. The angulating hip stem 140 includes a proximal end 142 and a distal end 144 extending between a longitudinal axis. Neck 146 extends at an angle from the proximal end 142 of the stem 140. The neck 146 terminates at a free end 148 configured to support a femoral head component (not shown) in articulating with the pelvis. The implant 140 includes a distal stem or shank 150 with a medial side 152 and a lateral side 154. The implant 140 includes an angulating body 156 near the proximal end 142 of the implant 140. The angulating body 156 may comprise a corner section or proximal lateral section of the implant 140. The angulating body 156 is configured to pivot laterally about pivot pin 158, thereby providing angular expansion configured to better fulfill the proximal metaphasis of the femur.

The angulating body 156 is articulatable via actuation assembly 160. The articulation assembly 160 includes a threaded ramp shaft 162 and a ramp body 164. A channel 166 extends downward into the implant 140 from the proximal end 142. The threaded ramp shaft 162 is receivable in the channel 166. When rotated, the threaded ramp shaft 162 translates in the proximal or distal direction. This translation, in turn, articulates the ramp body 164 to push against a corresponding ramp 168 on the medial side of the angulating body 156 to create expansion. The dowel pin 158 is in place to secure all components together. When the stem 140 is entirely unexpanded, the ramp body 164 secures the angulating body 156 ensuring all components are self-retaining. When expanded, the angulating body 156 pivots laterally outward about the pin 158, thereby providing an enhanced fit in the bone.

The expandable hip stems described herein may provide the surgeon with a prosthesis that can be adjusted to offer a more custom fit per the patient's needs. The fixation expandable stems can offer is greater than that of a press fit due to the forces applied to the metaphysis and diaphysis of the femur as expansion occurs. The expandable stems also offer fixation that could be located further distally into the diaphysis in the case that a revision hip procedure with a compromised metaphysis is being performed. When extraction of the stem may be warranted, the self-retaining feature of the stems may avoid the need to remove extensive cancellous/cortical bone or to conduct an extended trochanteric osteotomy.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all components of the various devices disclosed above may be combined or modified in any suitable configuration.

What is claimed is:
1. An implant for a hip arthroplasty comprising:
   a proximal body having a neck terminating at a free end and a channel extending therethrough;
   a distal stem having a proximal portion coupled to the proximal body, a distal portion terminating at a conical end, and a channel extending through the distal stem aligned with the channel of the proximal body;

a plurality of expandable bodies positioned around the distal stem, each expandable body having an inner surface facing toward the distal stem and an outer surface defining an outer diameter; and an actuation assembly for moving the plurality of expandable bodies, wherein the plurality of expandable bodies have a collapsed configuration and an expanded configuration such that the plurality of expandable bodies expand radially outward away from one another, thereby enlarging the outer diameter;

wherein the actuation assembly includes a ramp body with one or more ramp surfaces configured to engage with one or more corresponding ramp surfaces along the inner surfaces of the expandable bodies;

wherein the ramp body includes a single conical ramp.

2. The implant of claim 1, wherein the ramp body includes a pair of opposed flat ramp surfaces.

3. The implant of claim 1, wherein the actuation assembly includes a head portion and a threaded shaft that terminates at a distal end, and the threaded shaft is receivable through the channel in the distal stem.

4. The implant of claim 3, wherein rotation of the threaded shaft translates a ramp body distally through the distal stem, thereby expanding the expandable bodies radially outward.

5. The implant of claim 3, wherein the actuation assembly includes a plurality of extension springs aligned perpendicular to a longitudinal axis of the threaded shaft, and wherein the extension springs are configured to pull the expandable bodies inward toward the distal stem.

6. An implant for a hip arthroplasty comprising:

a proximal body having a neck terminating at a free end and a channel extending therethrough;

a distal stem having a proximal portion coupled to the proximal body, a distal portion terminating at a conical end, and a channel extending through the distal stem aligned coaxially with the channel of the proximal body;

a plurality of expandable bodies positioned around the distal stem, each expandable body having an inner surface facing toward the distal stem and an outer surface; and an actuation assembly including a threaded shaft and a ramp body for moving the plurality of expandable bodies, wherein rotation of the threaded shaft translates the ramp body distally, thereby expanding the expandable bodies radially outward.

7. The implant of claim 6, wherein the threaded shaft includes a head portion retained in the distal stem with an internal retaining ring, thereby ensuring the threaded shaft maintains its position within the distal stem while the ramp body translates.

8. The implant of claim 7, wherein the ramp body includes a collar seated inside a recess in the channel in the distal stem and a pair of opposed flat ramp surfaces configured to engage with corresponding flat ramp surfaces along the inner surfaces of the expandable bodies.

9. The implant of claim 7, wherein the threaded shaft is positioned through the ramp body and terminates at a distal end connected to the conical end of the distal stem.

10. The implant of claim 6, wherein the ramp body includes a single conical ramp positioned at a distal end of the threaded shaft configured to engage with corresponding ramp surfaces along the inner surfaces of the expandable bodies.

* * * * *